(12) United States Patent  
Rogers et al.

(10) Patent No.: US 8,218,146 B2  
(45) Date of Patent: Jul. 10, 2012

(54) SYSTEM AND METHOD FOR DETECTING A TARGET SUBSTANCE

(75) Inventors: Mark E. Rogers, Haymarket, VA (US); Paul L. Thee, Haymarket, VA (US); Richard A. Rosenthal, Leesburg, VA (US); Paul D. Biernacki, Ashburn, VA (US)

(73) Assignee: Northrop Grumman Systems Corporation, Falls Church, VA (US)

( * ) Notice: Subject to any disclaimer, the term of this patent is extended or adjusted under 35 U.S.C. 154(b) by 296 days.

(21) Appl. No.: 12/379,181

(22) Filed: Feb. 13, 2009

(65) Prior Publication Data

US 2010/0208267 A1    Aug. 19, 2010

(51) Int. Cl.  
*G01N 21/00* (2006.01)

(52) U.S. Cl. ......... 356/432; 356/433; 356/438; 356/326

(58) Field of Classification Search .......... 356/432–440, 356/300, 318, 301, 319, 326; 436/525, 71  
See application file for complete search history.

(56) References Cited

U.S. PATENT DOCUMENTS

| | | | |
|---|---|---|---|
| 2004/0252300 A1* | 12/2004 | Slater | 356/318 |
| 2005/0250212 A1* | 11/2005 | Azizian | 436/71 |
| 2006/0164633 A1* | 7/2006 | Koshoubu et al. | 356/300 |
| 2008/0180655 A1* | 7/2008 | Bruch et al. | 356/73 |
| 2009/0117669 A1* | 5/2009 | Yamamichi et al. | 436/525 |
| 2010/0098125 A1* | 4/2010 | Bianchi et al. | 372/40 |
| 2011/0069292 A1* | 3/2011 | Den Boef | 355/67 |

* cited by examiner

*Primary Examiner* — Hoa Pham  
(74) *Attorney, Agent, or Firm* — Andrews Kurth LLP

(57) ABSTRACT

A system and a method for detecting the existence of a target substance, the system includes a laser with a broad spectral output and a detector for detecting an absorption spectrum of a laser beam from the laser. The method includes emitting a laser beam into the atmosphere using a laser light with a broad spectral output; measuring the absorption spectrum of said laser beam; comparing the absorption spectrum to known absorption spectrums for target substances using a detector; and detecting the existence of a target substance.

14 Claims, 9 Drawing Sheets

SYSTEM AND METHOD FOR DETECTING A TARGET SUBSTANCE

BACKGROUND

Public screening is conducted at critical transportation and entry points. Most screening is conducted at airports, seaports, border crossings, high value civil infrastructure installations, and military bases. Currently employed methods to screen people against terrorist acts include physical searches, physical samples, and portal detection techniques to detect targets such as illegal drugs, explosives, and weapons.

In an example of present detection techniques in the laboratory, substance detection targets are identified by directing single-wavelength laser beams toward persons or specific areas. The presence of a target substance on the person or in the specific area is measured using spectroscopy methods.

Current detection devices employ various spectroscopy methods for detecting such target substances. Most present methods employ single-wavelength lasers to detect targets. The use of single-wavelength lasers exhibits shortcomings such as the occurrence of false positives and a failure to detect target substances due to an inherent reliance on a few data points from which to determine the existence of target substances. Accordingly, there is a need to provide an improved method of detecting target substances.

SUMMARY

An advantage of the embodiments described herein is that they overcome the disadvantages of the prior art. Another advantage of certain embodiments is the improved ability to remotely detect target substances via spectroscopy.

These advantages and others are achieved by a system for detecting the existence of a target substance. The system includes a laser with a broad spectral output for emitting a laser beam with a broad spectrum towards a target area from which the laser beam is reflected or transmitted. The system further includes a detector for detecting an absorption spectrum of the reflected laser beam from the laser. The detector receives the reflected laser beam, measures the absorption spectrum of the reflected laser beam, compares the absorption spectrum to known absorption spectrums for target substances, and determines if a target substance is present in the target area based on the comparison.

These advantages and others are also achieved by a method for detecting the existence of a target substance. The method includes emitting a laser beam towards a target area using a laser with a broad spectral output and receiving a reflected laser beam from the target area. The method further includes measuring the absorption spectrum of the reflected laser beam, comparing the absorption spectrum to known absorption spectrums for target substances using a detector, and determining whether a target substance is present in the target area based on the comparison.

These advantages and others are also achieved by a computer-readable medium comprising instructions for detecting the existence of a target substance, wherein the instructions include emitting a laser beam towards a target area using a laser with a broad spectral output and receiving a reflected laser beam from the target area. The instructions further include measuring the absorption spectrum of the reflected laser beam, comparing the absorption spectrum to known absorption spectrums for target substances using a detector, and determining whether a target substance is present in the target area based on the comparison.

DESCRIPTION OF THE DRAWINGS

The detailed description will refer to the following drawings, wherein like numerals refer to like elements, and wherein.

DETAILED DESCRIPTION

Figure 1:
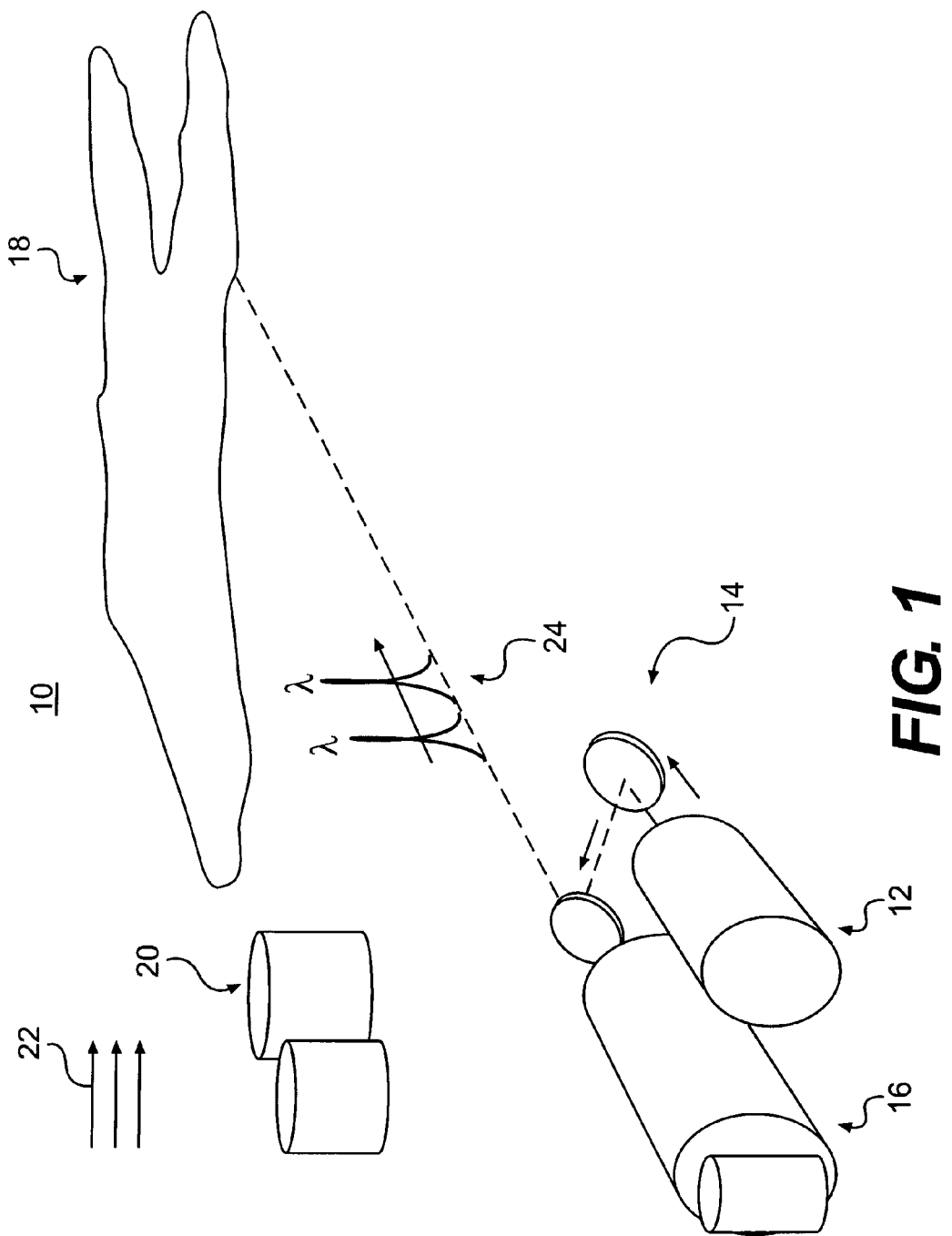
FIG. 1 shows a perspective view of an embodiment of the system for detecting a target substance sending output signals.

Described herein are a system and method for detecting a target substance. Applications of embodiments of the system and method directly relate to the identification and apprehension of potential individual bombers, specifically suicide bombers. Suicide bombers may be detected by vapors that the bombs substances emit. It is an advantage of the system that the system can remotely and quickly detect certain characteristics that correlate to a targeted individual's intention so that a mitigation strategy may be devised to stop an attack. Dangerous substances, such as a bomb found on a person or placed in a public space, can be detected by the signatures of their chemical molecules. The target substances examples include, but are not limited to, chemical warfare agents (CWA), non-traditional agents (NTAs), dusty agents (DAs), toxic industrial chemical (TIC) vapors, low vapor pressure chemicals (LVPCs), explosives, explosives and their related compounds, and residues thereof.

Examples of CWA includes, but are not limited to, nerve agents such as GA (Tabun, ethyl N,N-dimethyl phosphoramidocyanidate), GB (Sarin, isopropyl-methylphosphorofluoridate), GD (Soman, Trimethylpropylmethylphosphorofluoridate), GF (cyclohexyl-methylphosphorofluoridate) and VX (o-ethyl S-[2-(diiospropylamino)ethyl]methylphosphorofluoridate); vesicants such as HD (mustard, bis-2-chlorethyl sulfide), CX (Phosgene oxime, dichloroformoxime), and L (Lewisite, J-chlorovinyldichloroarsine); cyanides such as AC (Hydrocyanic acid) and CK (Cyanogen chloride); pulmonary agents such as CG (phosgene, carbonyl chloride) and DP (Diphosgene, trichloromethylchlorformate).

NTAs and DAs are CWAs dispersed as either a liquid or particulate aerosol. For example, dusty mustard is composed of mustard agent (liquid) dispersed onto fine particulates of silica.

Examples of TIC can be found on U.S. Environmental Protection Agency's reference list of toxic compounds (*Alphabetical Order List of Extremely Hazardous Substances*, section 302 of EPCRA).

The term "LVPCs" refers to those chemicals that, at atmospheric temperature and pressure, only an intangible level, if any, of the sample exists in the gaseous and/or vapor phase and as such the sample has, at atmospheric temperature and pressure, a vapor pressure significantly less than water.

Examples of LVPCs include, but are not limited to, Novichock agents, dusty agents, pesticides, and other toxic chemicals with vapor pressures less than $10^{-4}$ torr.

Examples of explosives include, but are not limited to, nitroglycerin-based powders, ammonium nitrate/fuel oil mixtures (ANFO), Trinitrotoluene (TNT), Pentaerythritoltetranitrate (PETN), Cyclotrimethylenetrinitramine (RDX), and Cyclotetramethylene-tetranitramine (HMX). Explosive related compounds include, but are not limited to, residual raw materials, manufacturing byproducts and degradation products.

Specific molecular species have unique vibration modes that emit and absorb certain wavelengths in the infrared portion of the electromagnetic spectrum. The target substances can be detected via spectroscopy by their unique vibration modes.

Remote spectroscopy, using embodiments of the system and method for detecting a target substance, is a solution to finding and identifying chemical molecules at a distance that will indicate the presence of dangerous materials. The embodiments may be placed at remote sites to continuously scan the atmosphere in areas of concern for the transport of dangerous materials.

Additionally, an embodiment of the system and method for detecting a target substance may include a remote spectroscopy sensing system for safety and security. Such a system may be capable of detecting many substances that might indicate malicious intent. Indicator materials may include dangerous materials themselves such as explosives and direct or indirect chemical indicators of personal anxiety or stress such as alcohol or drugs. Remote sensing techniques for these indicators may detect and identify aerosols or gas vapors from the substances.

Referring now to FIG. 1, shown is a perspective view of an embodiment of system 10 for detecting a target substance. System 10 is shown sending output signals toward a preselected area (the "target area"). The embodiment shown includes pulsed broad spectral output laser 12, steering mirrors 14, and detector 16. The pulsed broad spectral output laser 12 sends pulsed laser beams toward a gaseous plume 18 from an emission source 20 or a into the atmosphere to periodically monitor an area for target substances. The steering mirrors 14 steer the laser beams toward a target area, which can be a gaseous plume created by a wind source 22 from an emission source 20 or an identified area of the atmosphere. The pulsed broad spectral output laser 12 shown sends laser beams in a broadband spectrum 24 towards the target area for absorption into the atmosphere or gaseous plume 18. The pulsed broad spectral output laser 12 is capable of sending laser beams in a broad set of continuous wavelengths simultaneously.

Figure 2:
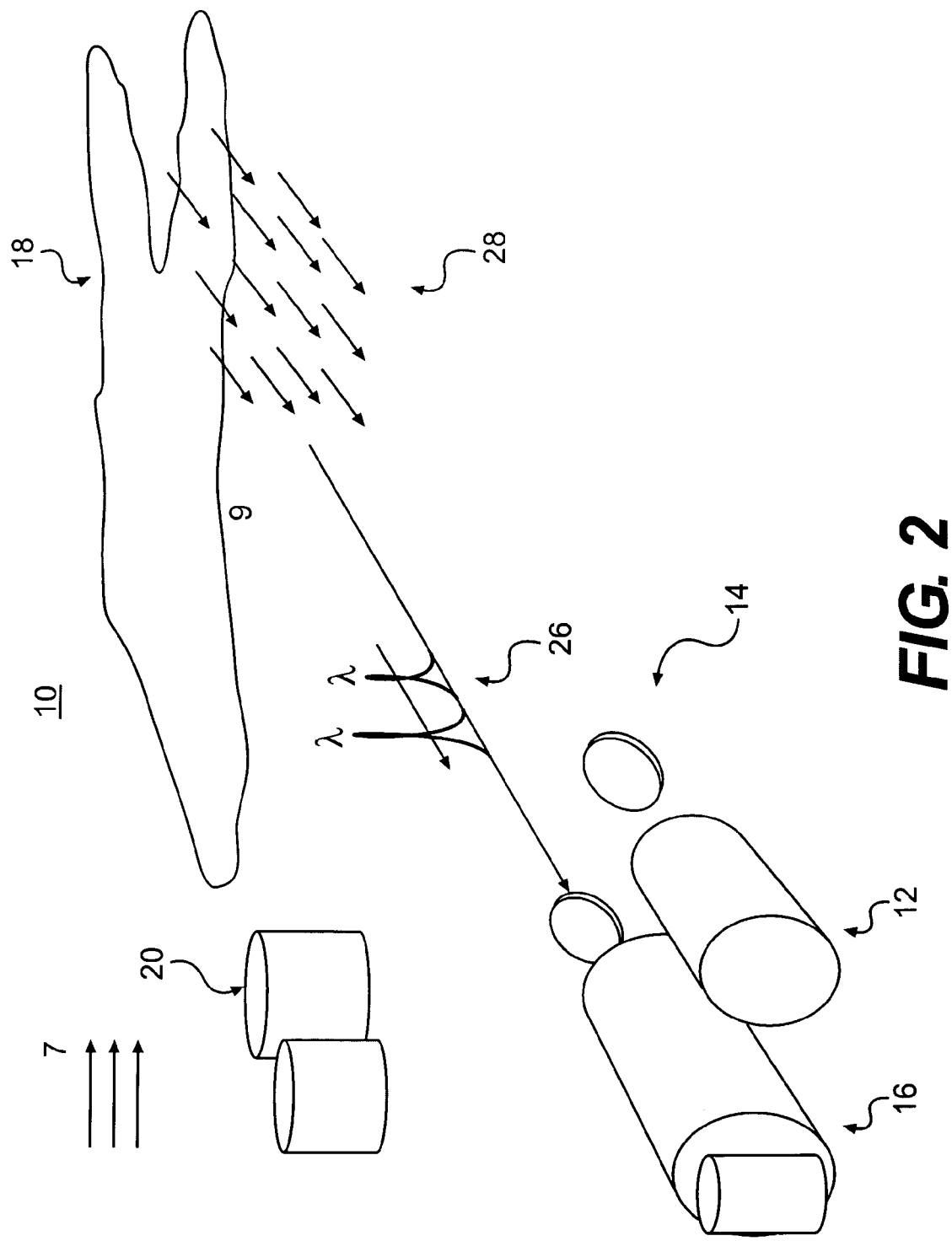
FIG. 2 shows a perspective view of an embodiment of the system for detecting a target substance receiving input signals.

Referring now to FIG. 2, shown is a perspective view of an embodiment of system 10 for detecting a target substance. System 10 is shown receiving input signals 26. The input signals 26 comprise the return signals, backscattered, or reflected, by particles along the beam path to the mercury cadmium telluride, lead sulfide, or similar detector 16. The detector is usually highly sensitive and can detect the backscattered light 28. These return signals are reflected by dust particles and aerosols that act as weak reflectors or by background solid objects such as a wall. The pulsed broad spectral output laser beam causes a set of absorption line signals to be returned to the detector. Embodiments of the system use spectroscopy to detect a target substance. Embodiments of the system 10 may use spectroscopy remotely where the detector 16 is placed at a distance from a target area. Spectroscopy, more particularly, absorption spectroscopy, is a technique in which the power of a beam of light at a broad continuous set of wavelengths is measured before and after interaction with a sample, and is compared. This technique is different from Differential Absorption Light detection and ranging (DIAL) method which uses a differential return from only two closely spaced wavelengths, one of which is strongly absorbed by the target gas. The size of the return signal from DIAL at different distances along the laser beam path indicates the concentration of absorption of substances or emissions from a source. This method employs a broad continuous spectrum of laser output wavelengths to detection absorption at many wavelengths instantaneously.

This measurement technique using a broad continuous laser spectrum relies on the unique "fingerprint" absorption spectrum of each molecule in a target substance. The term "fingerprint" refers to the absorption spectrum that results from the absorption of light from a laser that is specific to each target substance. An absorption measurement is made by a detector at various absorption wavelengths The concentrations can be converted into mass emissions by making a series of scans along different lines within a plume of a target substance and combining these with meteorological data. These measurements are then used to produce a mass emission profile for a site, such as an oil refinery.

The primary spectroscopic method employed by this system and method for detecting a target substance is overtone absorption spectroscopy.

Overtone absorption occurs when a higher energy laser photon is absorbed by the substance to be sampled, thereby exciting multiple vibrational states of the substance simultaneously. Measurements can be taken of the absorption of the input laser photon in the reflected or transmitted spectrum.

Figure 3:
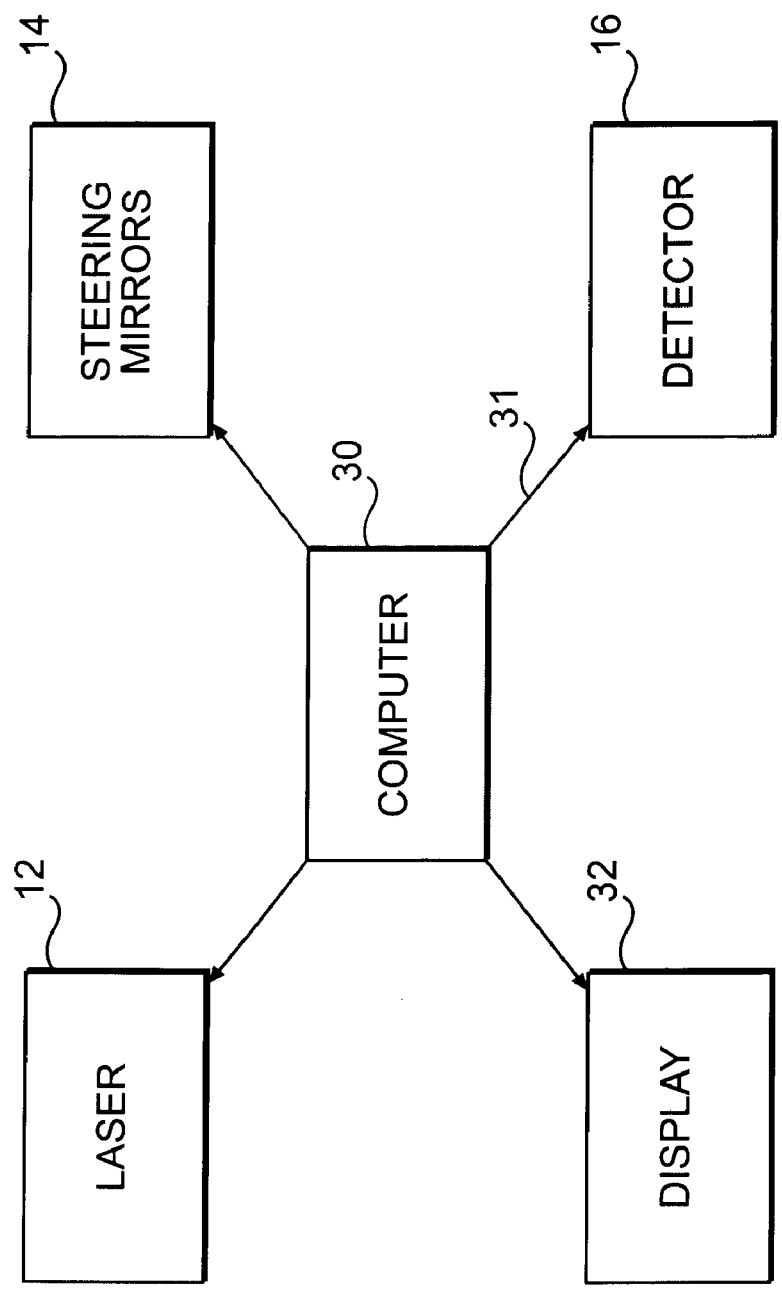
FIG. 3 shows a block diagram of the components of an embodiment of the system for detecting a target substance.

Referring now to FIG. 3, shown is a schematic diagram of components of an embodiment of system 10 for detecting the existence of a target substance. The components include a computer 30, laser 12, steering mirrors 14 and detector 16. The computer 30 directs the laser 12 to transmit a laser beam towards an emissions cloud or other target area. The computer commands can be generated manually or via a computer program. The computer also commands the steering mirrors 14 to direct the laser beam towards the target area. The detector 16 collects and sends absorption data to the computer 30 for processing. The absorption data outputted from the detector 16 is transferred to the computer 30 via a wired or wireless communication path 31. The computer 30 analyzes the absorption data, e.g., as described above, by comparing the return signal to the original laser beam. The computer 30 outputs data sharing the analysis results. If present, the data will show the presence of target substances in the target area. The output data of a target substance and/or an analysis of a scanned area may be displayed on a display device 32 connected to the computer 30. The display device 32 may be remote from the computer.

Figure 4:
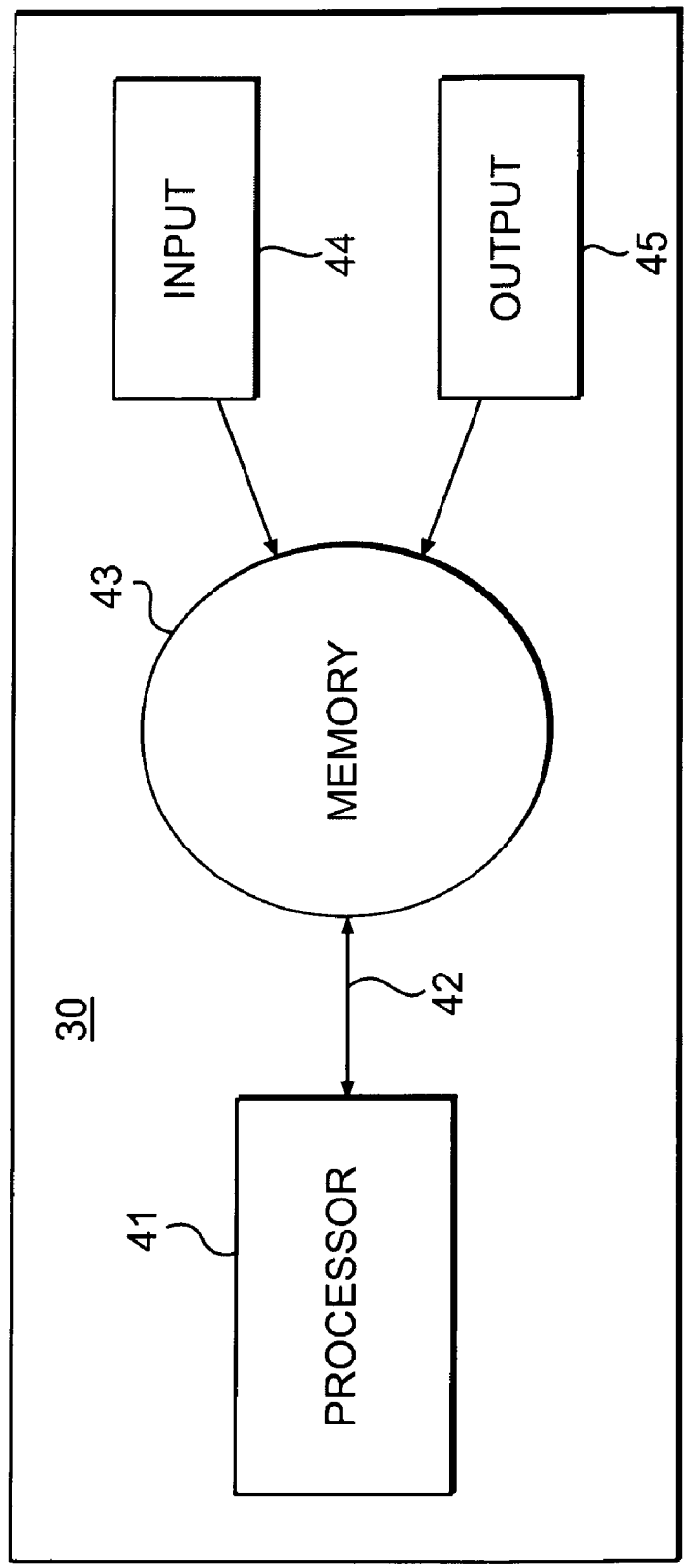
FIG. 4 shows a block diagram of the control system of an embodiment of the system for detecting a target substance.

Referring now to FIG. 4, shown is a schematic diagram of the computer 30 of an embodiment of the system for detecting the existence of a target substance. The computer includes a control unit 40 including a processor 41 and datapath 42 for communicating data to and from memory 43 and the secondary storage. The computer further includes an input component 44 and output component 45 for communicating with the components of the system and method for detecting a target substance. The computer may be placed within the detector 16 or may be placed remotely from the laser 12 and detector 16. The data outputted by the detector 16 is sent to the computer system 30 via the input component 44 and sent via the datapath 42 to the memory which is accessible by the processor 41, via the datapath 42. After the data from the detector is processed by the processor 41, the processor 41 outputs and/or stores the resulting data in and/or on computer-readable media (e.g., compact disk, digital video disk, floppy disk, random access memory and the like). The output data may show the existence of a target substance and/or identify the target substance. The output data may also identify all of the substances in the target area.

Figure 5:
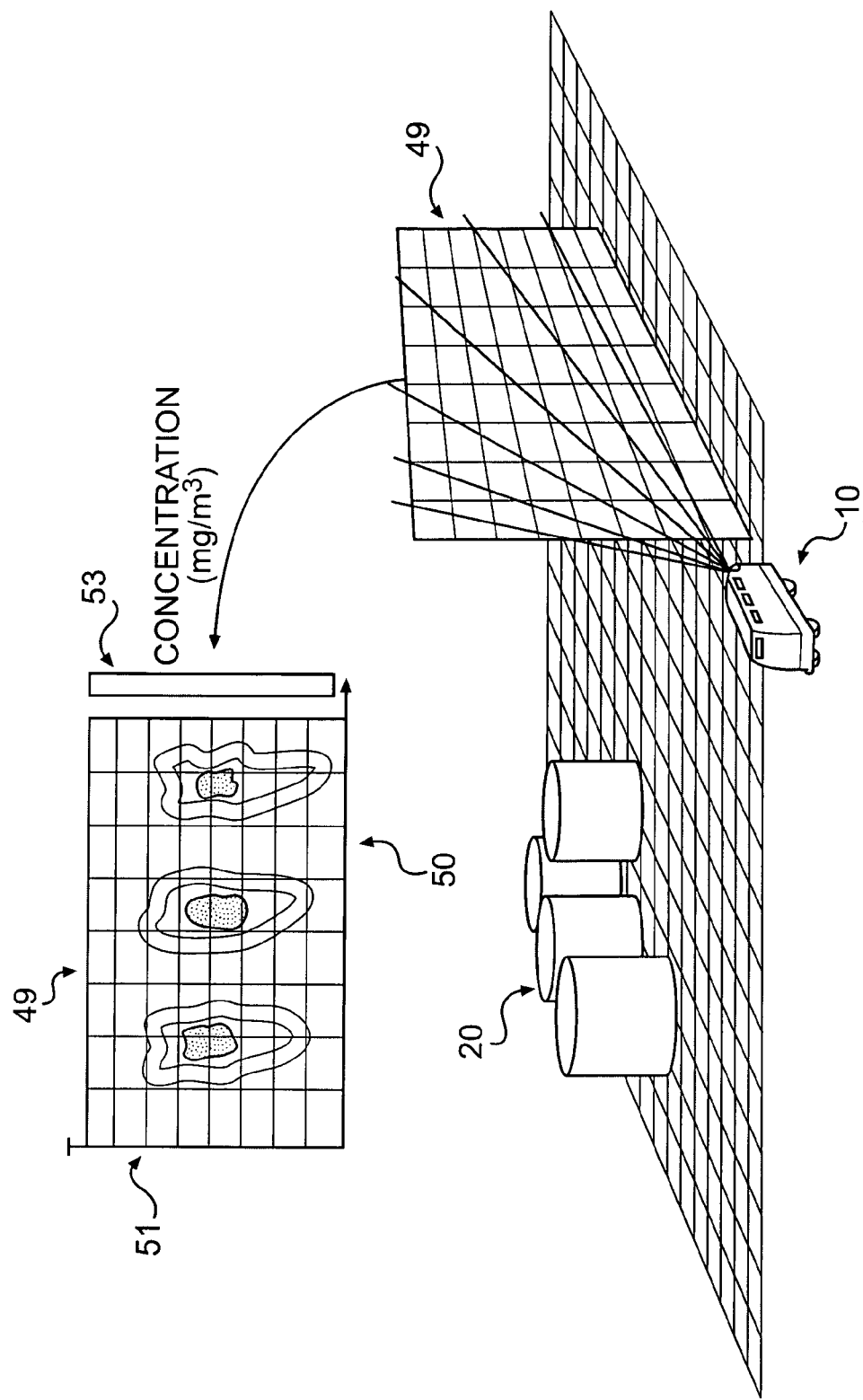
FIG. 5 shows a perspective view of an embodiment of the system for detecting a target substance showing a graph of an emissions concentration profile.

Referring now to FIG. 5, shown is a perspective view of an embodiment of the system 10 for detecting a target substance. The system 10 is shown scanning an area. The system 10 in this example is located in a mobile unit. Also shown is a graph of a sample mass emission concentration profile 49. A mass emission concentration profile can be created when the concentration of the absorption of a laser beam is measured and combined with meteorological data. The x-axis 50 of the mass emission concentration profile 49 shows the range in meters of the concentration of absorption of a laser beam by emissions from an emission source 20. The y-axis 51 of the sample mass emissions concentration profile shows the concentration of absorption over height of the laser beam in meters. The concentrations are shown as milligrams per cubic meter ($mg/m^3$) 53. The emissions profiles of a site can be stored in memory for a computer to access in order to compare newly created emission profiles of a site to old profiles to detect abnormalities such as the existence of a substance that is not normally found at a site.

Figure 6A:
FIGS. 6A-6C show graphs of a sample infrared absorption spectrum of a high explosive substance.
Figure 6B:
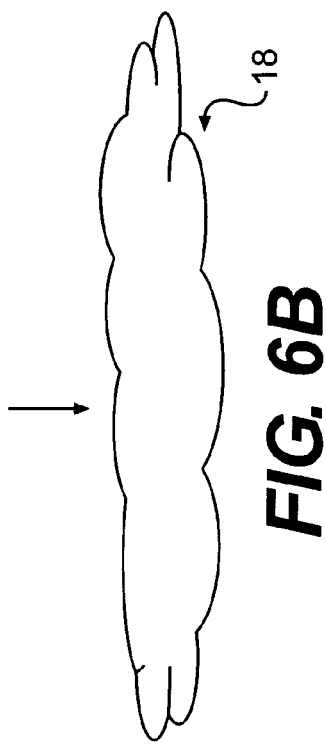
Figure 6C:
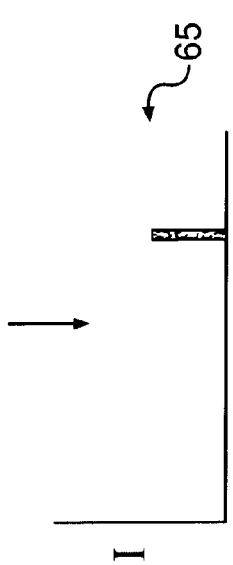

Referring now to FIGS. 6A-6C, shown are graphical representations of absorption line data of a single-line laser from a spectrometer. FIG. 6A shows a graph of a standard single-line laser beam 60 prior to absorption by an emissions cloud or gaseous plume 18. FIG. 6B shows an emissions cloud or gaseous plume 18. FIG. 6C shows a graph of a single line of absorption 65 by an emissions cloud or gaseous plume 18 of a single-line laser beam. A single line of absorption from a single-line laser beam provides an ambiguous signature for a target substance or chemical because there are not enough data points to create a unique signature for a target substance. Thus, absorption spectrum data from a single-line laser beam is an unreliable indicator for the presence of target substances in a target area.

Figure 7A:
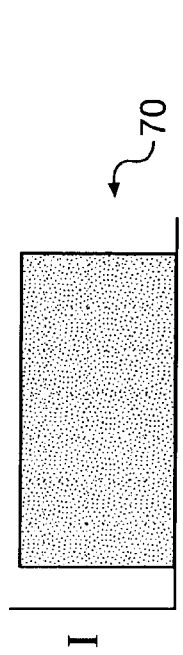
FIGS. 7A-7C show a graphs of a sample infrared absorption spectrum of ethyl alcohol.
Figure 7B:
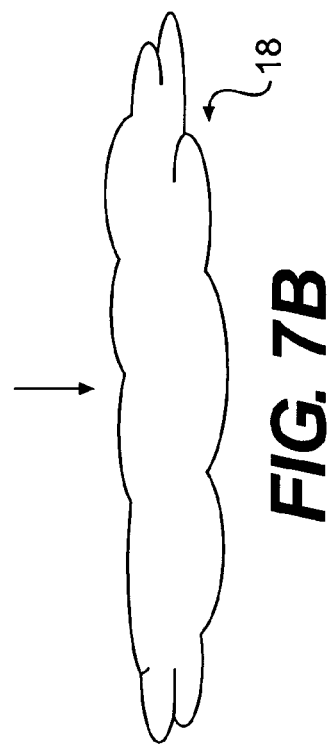
Figure 7C:
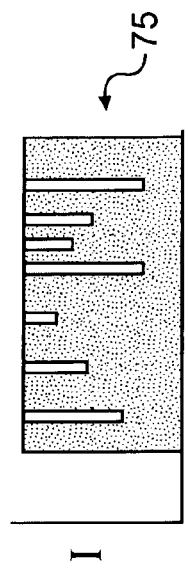

Referring now to FIG. 7A-7C, shown are graphical representations of an absorption spectrum of a pulsed broad spectral output laser 12 with a broad spectral output. In this example, the laser 12 with a broad spectral output is a supercontinuum laser. FIG. 7A shows a graph of a supercontinuum laser beam 70 prior to absorption by an emission cloud or gaseous plume 5. FIG. 7B shows an emissions cloud or gaseous plume 18. FIG. 7C shows a graph of data from a spectrometer showing the multiple lines of absorption 75 of the supercontinuum laser beam after absorption by the emission cloud or gaseous plume 18. The absorption spectrum from supercontinuum laser beams provides unique, identifying signatures for a target substances or chemicals. The unique signatures of the target substances enable a more accurate determination of the existence of a target substance. The unique signatures of target substances reduce the frequency of false positives and/or error when the system 10 is scanning a target area.

An embodiment of the system and method for detecting a target substance includes a white-light source that is spatially coherent, i.e. the supercontinuum laser. Supercontinuum laser light sources provide the unusual characteristic of a broad spectral output while retaining a high degree of spatial coherence, directionality, and or narrow beam width.

The supercontinuum laser can detect minute quantities of trace chemicals that may identify various security threats from a distance. Among the many advantages of such a laser are for the broadband nature of the light, the spatial coherence, the intensity of the beam, and the ability to provide a small, low-divergence beam. The directionality of the supercontinuum laser allows target discrimination. This enables the system to associate vapors from dangerous chemicals with specific persons. In application, the supercontinuum laser of system 10 is significantly faster than current systems. Moreover, by operating beyond 1.4 microns, the supercontinuum laser beam is invisible, enabling the spectral scanner, or detector, to remain undetected. This feature permits covert analysis of a target area.

Figure 8:
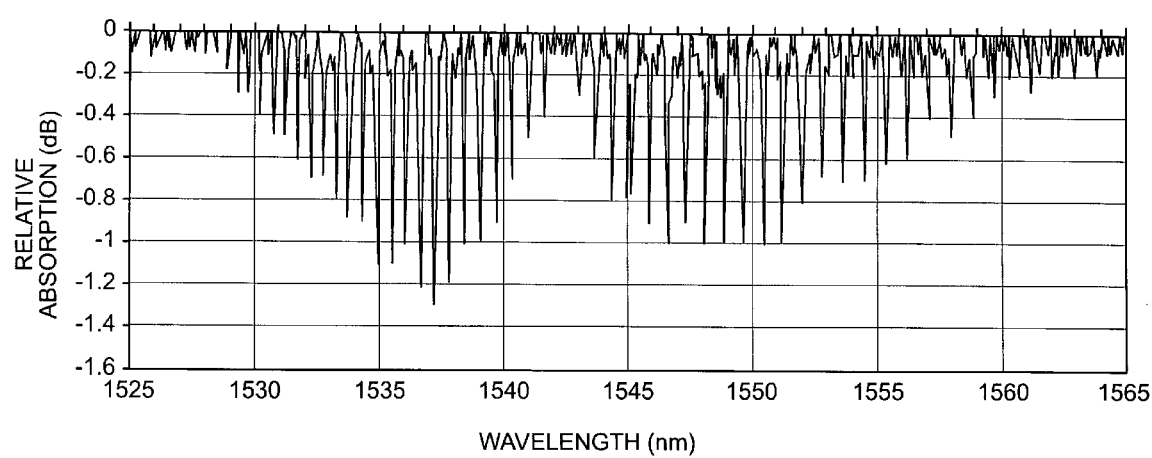
FIG. 8 shows a graph of a sample transmission spectrum of hydrogen cyanide gas.

FIG. 8 shows a graph of a sample of an actual transmission spectrum of hydrogen cyanide gas taken with the broadband supercontinuum laser spectroscopy described in the system 10 for detecting a target substance. The graph shows the relative absorption of the hydrogen cyanide gas in the target area on the y-axis and the wavelength of the gas on the x-axis.

Figure 9:
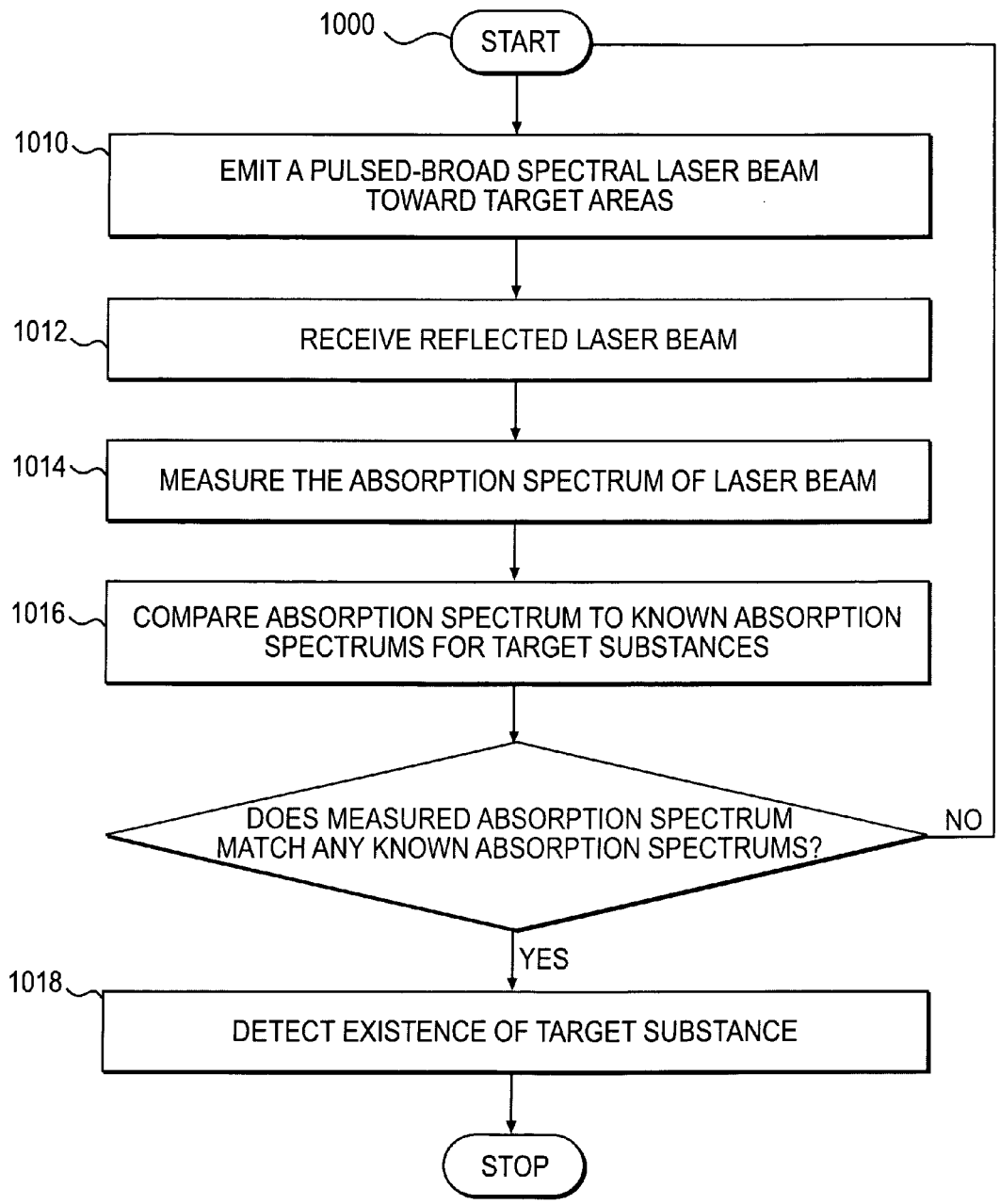
FIG. 9 shows a flow-chart of an embodiment of the method for detecting a target substance.

Referring now to FIG. 9, shown is a flow-chart of an embodiment of a method 1000 for detecting a target substance is shown. A pulsed laser beam is emitted from a laser light with a broad spectral output toward target areas, block 1010. The reflected wavelength of the laser beam is received, block 1012. The absorption spectrum of the laser beam is measured using spectroscopy, block 1014. The method 1000 may use various methods of spectroscopy and remote spectroscopy, including the spectroscopy methods described above. The method 1000 then compares the measured absorption spectrum to the known absorption spectrums for target substances, block 1016. From the comparison, a matching signature may be identified to determine the existence of a target substance, block 1018.

In an embodiment of method 1000, a supercontinuum laser is used to emit the pulsed laser beam, block 1010.

In an embodiment of method 1000 a computer processor is used to compare a measured absorption spectrum of a laser beam against known absorption spectrums for identifying target substances.

Figure 10:
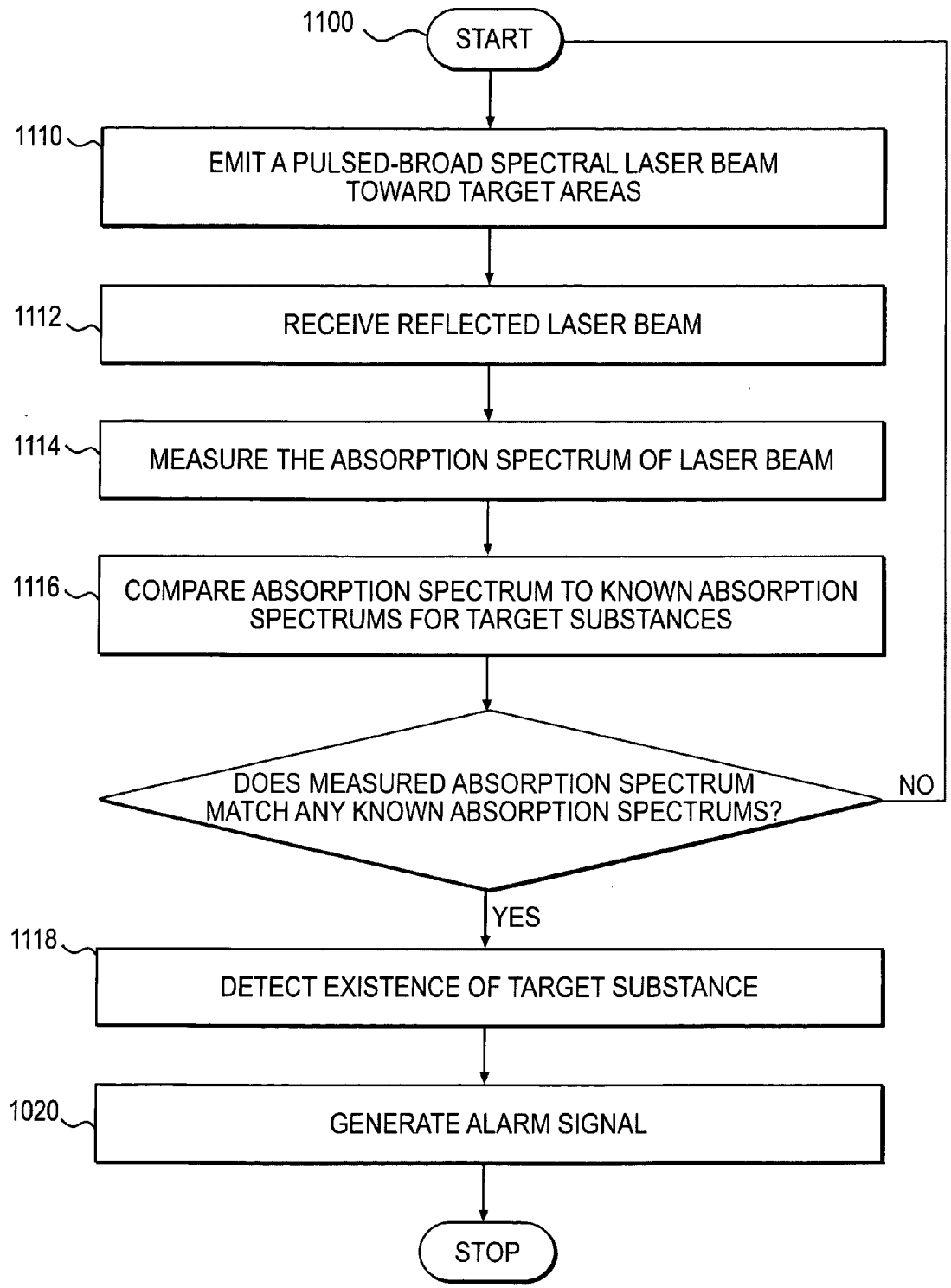
FIG. 10 shows a flow-chart of another embodiment of a method for detecting a target substance is shown.

Referring now to FIG. 10, shown is a flow-chart of another embodiment of a method 1100 for detecting a target substance is shown. A pulsed laser beam is emitted from a laser light with a broad spectral output toward target areas, block 1110. The reflected wavelength of the laser beam is received, block 1112. The absorption spectrum of the laser beam is measured, block 1114. The method then compares the measured absorption spectrum to the known absorption spectrums for target substances, block 1116. From the comparison, a matching signature may be identified to determine the existence of a target substance, block 1118. The method further includes generating an alarm signal 1120 to alert security personnel, for example, when the existence of a target substance is detected. Instructions for performing embodiments of the method for detecting a target substance may be stored on a computer-readable medium for execution by computer (such as computer 30).

The embodiments described herein more reliably measure the emissions of a target area and provides a system that has a high probability of detecting specific substances, while having a low probability of false alarm. The embodiments achieve these advantages by using a broad spectral measurement.

The terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated.

What is claimed is:

1. A method for detecting the existence of a target substance, the method comprising:
    emitting a spatially-coherent, low-divergence, narrow beam-width laser beam from a supercontinuum laser with a broad continuous spectrum of laser output wavelengths towards a target area;
    commanding a steering minor to direct the laser beam towards the target area;
    receiving a reflected supercontinuum laser beam from the target area;
    measuring the absorption spectrum of said reflected supercontinuum laser beam, wherein the absorption spectrum of said supercontinuum laser beam provides unique, identifying signatures for a target substance;
    comparing the absorption spectrum to known absorption spectrums for target substances; and
    determining if a target substance is present in the target area based on the comparison.

2. The method of claim 1 wherein the laser beam is a pulsed laser beam.

3. The method of claim 1 further comprising a computer comparing the absorption spectrun to known absorption spectrums for target substances.

4. The method of claim 1 further comprising generating an alarm signal upon determining the existence of a target substance.

5. The method of claim 1 wherein the supercontinuum laser sends laser beams in a broad set of continuous wavelengths simultaneously.

6. A method for remotely detecting the existence of a target substance, the method comprising:
    emitting a spatially-coherent, low-divergence, narrow beam-width laser beam from a supercontinuum laser with a broad continuous spectrum of laser output wavelengths towards a target area from which the laser beam is reflected or transmitted;
    commanding a steering mirror to direct the laser beam towards the target area;
    receiving a reflected or transmitted supercontinuum laser beam;
    measuring the absorption spectrum of said supercontinuum laser beam, wherein the absorption spectrum of the supercontinuum laser beam provides unique, identifying signatures for a target substance;
    comparing the absorption spectrum to known absorption spectrums for target substances; and
    determining if a target substance is present in the target area based on the comparison.

7. The method of claim 6 further comprising displaying processed absorption spectrum data on a display medium.

8. A system for detecting the existence of a target substance, the system comprising:
    a supercontinuum laser with a broad spectral output, wherein the laser is configured to emit a spatially-coherent, low-divergence, narrow beam-width laser beam with a broad spectrum towards a target area from which the laser beam is reflected or transmitted;
    a steering mirror for directing the laser beam towards the target area;
    a detector for detecting an absorption spectrum of the laser beam, wherein the absorption spectrum of the laser beam provides unique, identifying signatures for a target substance;
    wherein the detector receives the reflected or transmitted laser beam, measures the absorption spectrum of the reflected laser beam, compares the absorption spectrum to known absorption spectrums for target substances, and determines if a target substance is present in the target area based on the comparison.

9. The system of claim 8 wherein the detector comprises a HgCdTe, PbS detector.

10. The system of claim 8 further comprising a computer for processing the data from the detector and directing the laser towards the atmosphere.

11. The system of claim 10 wherein the computer is located within the detector.

12. The system of 10 further comprising a display for displaying the absorption spectrum data.

13. A computer readable-medium comprising instructions for detecting the existence of a target substance, by:
    emitting a spatially-coherent, low-divergence, narrow beam-width laser beam from a supercontinuum laser with a broad continuous spectrum of laser output wavelengths towards a target area;
    commanding a steering minor to direct the laser beam towards the target area;
    receiving a reflected supercontinuum laser beam from the target area;
    measuring the absorption spectrum of said reflected supercontinuum laser beam, wherein the absorption spectrum of said supercontinuum laser beam provides unique, identifying signatures for a target substance;
    comparing the absorption spectrum to known absorption spectrums for target substances; and
    determining if a target substance is present in the target area based on the comparison.

14. The computer readable-medium of claim 13 wherein the laser beam is a pulsed laser beam.

* * * * *